United States Patent [19]

Colon et al.

[11] 4,263,466

[45] Apr. 21, 1981

[54] COUPLING OF ARYL AND HETEROARYL MONO CHLORIDES

[75] Inventors: Ismael Colon, Middlesex; Louis M. Maresca, Belle Mead; George T. Kwiatkowski, Green Brook, all of N.J.

[73] Assignee: Union Carbide Corporation, New York, N.Y.

[21] Appl. No.: 72,310

[22] Filed: Sep. 11, 1979

Related U.S. Application Data

[63] Continuation-in-part of Ser. No. 955,758, Oct. 30, 1978, abandoned.

[51] Int. Cl.$^3$ ................................................ C07C 1/26
[52] U.S. Cl. ..................................... 585/421; 252/459
[58] Field of Search ......................... 585/421; 252/459

[56] References Cited

U.S. PATENT DOCUMENTS

| | | | |
|---|---|---|---|
| 3,414,629 | 12/1968 | McCall et al. | 260/666 |
| 3,641,175 | 2/1972 | Wilke et al. | 260/666 |
| 3,661,882 | 5/1972 | Hawkins et al. | 260/94.3 |
| 3,736,264 | 5/1973 | Chauvin | 252/429 R |
| 3,856,868 | 12/1974 | Fahey | 260/666 |
| 3,859,327 | 1/1975 | Wells | 260/465.8 R |
| 4,000,211 | 12/1976 | Smith et al. | 252/430 |

FOREIGN PATENT DOCUMENTS 52-154900 12/1977 Japan .

OTHER PUBLICATIONS

Michio Zembayashi et al., Tetrahedron Letters, No. 47, pp. 4089–4092, 1977.
Takakazu Yamamoto, Bull. Chem. Soc. Japan 51 (7), pp. 2091–2097, 1978.

*Primary Examiner*—Veronica O'Keefe
*Attorney, Agent, or Firm*—Donald M. Papuga

[57] ABSTRACT

Aryl and heteroaryl mono chlorides are coupled in an aprotic solvent under an inert atmosphere by a catalyst mixture of a nickel compound and a ligand in the presence of a reducing metal.

20 Claims, No Drawings

COUPLING OF ARYL AND HETEROARYL MONO CHLORIDES

This application is a Continuation-In-Part of copending U.S. Pat. application Ser. No. 955,758, filed Oct. 30, 1978, now abandoned.

BACKGROUND OF THE INVENTION

This invention pertains to a method of coupling aryl and heteroaryl mono chlorides and more particularly to the use of a catalyst mixture of an anhydrous nickel compound and a ligand in the presence of a reducing metal in a dipolar aprotic solvent. Also, this invention relates to novel catalyst compositions.

Reactions which form carbon-carbon bonds are few although they are extremely useful in organic synthesis. In the formation of these bonds involving aryl groups, coupling is usually accomplished through the use of a metal. The use of copper in the Ullman reaction is described in Chem. Rev. 38,139 (1946); 64, 613 (1964). The use of nickel complexes was described by M. F. Semmelhack, et al in J. Am. Chem. Soc., 93, 5908 (1971). The use of palladium complexes was described by F. R. S. Clark, et al, J. Chem. Soc. Perkin I, 121 (1975). The latter reactions with nickel or palladium complexes have the advantage of proceeding at moderate temperatures but are disadvantageous in that aryl chlorides were either completely unreactive or gave very poor yields.

SUMMARY OF THE INVENTION

A practical method of coupling aryl and heteroaryl mono chlorides having 4 to about 30 carbons has been found which comprises contacting said aryl mono chlorides in an aprotic solvent with a catalytic amount of a catalyst mixture comprising an anhydrous nickel compound and at least one ligand selected from the group consisting of a triaryl phosphine having 6 to about 14 carbons in each aryl moiety and an aromatic bidentate compound containing at least one ring nitrogen atom and about 5 to about 30 carbon atoms, in the presence of a reducing metal selected from the group consisting of zinc, magnesium or manganese, or mixtures thereof, at a temperature of from about 0° to about 250° C., wherein the ratio of gram atoms of nickel to moles of aryl mono chloride is in the range of about 0.0001 to about 0.5, the amount of ligand is about 0.1 to about 100 moles per gram atom of nickel and the amount of reducing metal is at least about 0.5 gram atoms per mole of reacted aryl mono chloride.

It was unexpected that this reaction would be effective for coupling aryl mono chlorides.

The coupled products of this invention can be used as heat transfer media, liquid crystal intermediates, fluorescent brighteners, or polymer additives.

The novel catalyst compositions comprise an anhydrous nickel compound and at least one ligand selected from the group consisting of a triaryl phosphine having 6 to about 14 carbons in each aryl moiety and an aromatic bidentate compound containing at least one ring nitrogen atom and about 5 to about 30 carbon atoms, a metal selected from magnesium or manganese, and a promoter selected from alkali, alkaline earth, zinc, magnesium, manganese and aluminum halides, sulfates or phosphates, wherein the amount of ligand is from about 0.1 to about 100 moles per gram atom of nickel, the amount of magnesium or manganese is at least about 1 gram atom per gram atom of nickel, and the amount of promoter is at least 0.1 mole per gram atom of nickel.

The coupling reaction takes place at temperatures of from about 0° to about 250° C., preferably from about 25° to about 120° C., and most preferably, from about 40° to about 80° C.

Pressure is not critical and so superatmospheric or subatmospheric pressures can be used as well as atmospheric pressure. Reaction is carried out in an inert atmosphere.

Reaction time is not critical since quantitative yields are often obtained in less than 2 hours. When inorganic salt promoters are used, reaction times of only a few minutes are required to achieve high yields of coupled aryl compounds. There are no maximum times since the reaction is essentially irreversible.

Preferred promoters include alkali, alkaline earth, zinc, magnesium, manganese and aluminum halides, or mixtures thereof. Iodides are particularly preferred. The amount of promoter, when used, can range from about 0.1 to about 1000 moles per gram atom of nickel with about 1 to about 100 moles of promoter being preferred. If desired one can also employ alkali, alkaline earth, zinc, magnesium, manganese, and aluminum sulfates or phosphates, or mixtures thereof as promoters.

Suitable nickel compounds are those reducible by organometallic and metal reducing agents. These compounds include nickel halides, that is, the chlorides, bromides and iodides, nickel sulfates, nickel phosphates, nickel carbonates, nickel salts of organic acids having 1 to 18 carbons, such as, nickel formate, nickel acetate, and nickel organic complexes such as nickel acetylacetone, dichloro-bis(triphenylphosphine) nickel (II) and the like; and nickel (0) compounds such as bis(1,5-cyclooctadiene) nickel, tetrakis(triphenylphosphine) nickel, and the like. The anion of the nickel compounds is unimportant and serves merely to provide nickel ion to the catalyst mixture, but it must not interfere with the reaction of the nickel compound with the ligand. The preferred anions are the halides.

Suitable triaryl phosphines include triphenylphosphine, triphenylphosphines containing alkyl or alkoxy substituents having up to about 8 carbon atoms, and unsubstituted or alkyl- and alkoxy-substituted trinaphthyl phosphines. Suitable bidentate compounds include 2,2'-bipyridyl, 1,10-phenanthroline, 1,8-naphthyridine, 2-methylaminopyridine, and the like.

Preferred aprotic solvents include dipolar solvents, such as dimethylacetamide, dimethylformamide, dimethylsulfoxide, sulfolane and the like. If desired these aprotic solvents can be mixed with lower polarity inert solvents, such as saturated aliphatic hydrocarbons, including pentanes, hexanes, dodecanes and the like; aromatic hydrocarbons, such as, benzene, toluene, xylenes and the like; and saturated aliphatic and cycloaliphatic ethers, such as, diethyl ether, diglyme, tetrahydrofuran and the like.

It is preferred that all solvents used in the practice of this invention be anhydrous.

Although magnesium and manganese metals can be used, zinc metal is the preferred metal in the process for coupling aryl mono chlorides. It is also preferred that the metal be in finely divided form with an average sieve size of 20 or finer when measured on the U.S. sieve scale.

Preparation of the novel catalyst composition is carried out conveniently by mixing the aforementioned nickel compound, ligand(s), promoter, magnesium and- /or manganese metals in the aprotic solvent under an inert atmosphere and heating from about 25° to about 60° C.

While not wishing to be bound by any scientific theory or explanation of the mechanism of the coupling reaction of this invention, it is believed that the combination of nickel compound, ligand and reducing metal provides nickel in a zero valent state, a form which in an anhydrous aprotic medium enables the coupling of aryl mono chlorides to take place in excellent yields.

The nickel (0) ligand complex believed to be the active catalyst can be formed in situ in the presence of an aryl chloride, or the catalyst can be preformed in situ prior to the addition of the aryl chloride. A method for the determination of zero valent nickel is described by C. A. Tolman, J. Am. Chem. Soc. 92, 2956 (1970).

The preferred ratio of gram atoms of nickel to moles of aryl chloride is about 0.001 to about 0.1.

The preferred ratio of ligand to nickel is about 1 to about 30 moles per gram atom of nickel.

Although the stoichiometric amount of reducing metal required in this coupling reaction is about 0.5 moles of reducing metal per mole of reacted aryl chloride, it is preferred to use equimolar or even greater than equimolar amounts of reducing metal to aryl chloride.

The preferred aryl mono chlorides used in this invention have the formula:

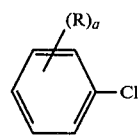

wherein R is independently selected from a monovalent inert radical such as alkyl, aryl, F, unsubstituted or substituted amino, —CN, —CHO, —Oaryl, —Oalkyl, —OCOaryl, —OCOalkyl, —COOalkyl, —COOaryl,

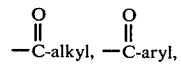

—$SO_2$—aryl or —$SO_2$—alkyl, —$SO_3$—alkyl, —$SO_3$aryl wherein the aryl contains 4 to about 30 carbon atoms, the alkyl contains 1 to about 8 carbon atoms and a is an integer having values of 0 to 4, with the proviso that no more than one R is in a position ortho to the Cl—containing ring carbon atoms. By inert radicals is meant radicals which do not interfere with the coupling reaction.

Another preferred mono chloride compound is a heteroaryl mono chloride wherein one or more of the carbon atoms of the benzene ring in formula (I) is replaced by a hetero atom such as N or P.

The invention is further described in the examples which follow. All parts and percentages are by weight unless otherwise specified.

EXAMPLE 1

In a 50 ml flask were placed 0.13 g of anhydrous nickel chloride, 2.0 g triphenylphosphine, and 2.0 g of zinc dust, which had been treated by washing with warm acetic acid then ether and dried on a vacuum line. The flask was sealed with a serum cap and purged with nitrogen for 30 minutes. Ten mls of dry DMAC (dimethylacetamide) was added and the flask was placed in an oil bath at 80° C. The solution was stirred by a magnetic bar and once the red-brown nickel (0) complex had formed, 2 ml of dry chlorobenzene were added. After 90 minutes the chlorobenzene had been converted quantitatively to biphenyl as determined by gas chromatography using toluene as an internal standard.

EXAMPLES 2–8

The following experiments were carried out according to Example 1, but 0.01 moles of the various promoter salts listed in Table 1 were also included.

TABLE 1

| Example No. | Salt | % Yield Biphenyl | Reaction |
|---|---|---|---|
| 2 | NaF | >99 | 80 min. |
| 3 | $Na_2SO_4$ | >99 | 65 |
| 4 | NaCl | >99 | 60 |
| 5 | NaBr | >99 | 20 |
| 6 | NaI | >99 | 4 |
| 7 | $ZnCl_2$ | 98 | 50 |
| 8 | $AlCl_3$ | 98 | 45 |

Compared to Example 1 it is seen in Example 2–8 that addition of the promoter salts reduces the reaction time by as much as a factor of 20 while maintaining essentially quantitative yields.

EXAMPLES 9–10

The following examples were carried out in accordance with Example 1 except that zinc was replaced by the metal listed in Table 2.

TABLE 2

| Example No. | Metal | % Yield Biphenyl | Reaction Time |
|---|---|---|---|
| 9 | Mg | >99 | 2 hours |
| 10 | Mn | >99 | 20 hours |

EXAMPLES 11–17

The following examples were carried out in accordance with Example 1 except that the substituted chlorobenzenes listed in Table 3 were used in place of chlorobenzene. Any additives not found in Example 1 are also included in Table 3.

TABLE 3

| No. | Reactant | Additive | % Conversion | Temp. C.° | Reaction Time |
|---|---|---|---|---|---|
| 11 | p-chlorophenyl-acetate | 1g NaBr | 80 | 70° | 100 minutes |
| 12 | p-chloro-aniline | — | 88 | 80° | 60 minutes |
| 13 | p-chloro-anisole | 1g NaBr | 93 | 70° | 90 minutes |
| 14 | p-chloro-toluene | 1g NaBr | 90 | 70° | 30 minutes |
| 15 | p-chloro-benzaldehyde | 1g NaBr | 94 | 70° | 55 minutes |
| 16 | p-chloro-acetophenone | 1g NaBr | 100 | 70° | 15 minutes |
| 17 | p-chloro-benzonitrile | 1g NaBr | 98 | 70° | 60 minutes |

It should be noted that in Examples 11–13 multiple products were obtained. These are listed in Table 4.

TABLE 4

| No. | Products | % Yield |
|---|---|---|
| 11 | 4,4'-diacetoxybiphenyl | 66 |
|    | 4-acetoxybiphenyl | 3 |

TABLE 4-continued

| No. | Products | % Yield |
|---|---|---|
|  | phenylacetate | 11 |
| 12 | 4,4'-diaminobiphenyl | 31 |
|  | 4-aminobiphenyl | 26 |
|  | biphenyl | 31 |
| 13 | 4,4'-dimethoxybiphenyl | 69 |
|  | 4-methoxybiphenyl | 19 |
|  | biphenyl | 5 |

EXAMPLES 18–21

The following experiments were performed in accordance with Example 1 except that nickel chloride was replaced by the nickel salts listed in Table 5 and 0.01 moles of NaI were included.

TABLE 5

| No. | Nickel Compound | % Conversion |
|---|---|---|
| 18 | nickel bromide | 91 |
| 19 | nickel iodide | 100 |
| 20 | nickel acetylacetone | 94 |
| 21 | nickle acetate | 99 |

EXAMPLE 22

Example 1 was repeated with the exception that the triphenylphosphine was replaced by an equivalent amount of tris(p-methoxyphenyl) phosphine. A 89% yield of biphenyl was obtained in 2 hours.

EXAMPLES 23–27

The following examples illustrate the use of an aromatic bidentate nitrogen compound in the coupling reaction.

EXAMPLE 23

0.13 g $NiCl_2$, 2.0 g zinc, 2.0 g triphenylphosphine, 1.0 g sodium iodide, and 0.2 g 2,2'-bipyridine were added to in a 50 ml flask. The flask was evacuated and filled with nitrogen and then 10 ml of dry DMAC and 2 ml p-chloroanisole were added. The reaction mixture was then stirred and reacted at 80°. After 75 min. the reaction was over as determined by disappearance of p-chloroanisole, and a 80% yield of 4,4'-dimethoxybiphenyl was obtained. In contrast to example number 13, a higher yield of coupled product was obtained and there were no other biphenyls produced. The addition of bipyridine appears to suppress the side reaction leading to these other products. The only other significant product produced was anisole.

EXAMPLE 24

0.13 g $NiCl_2$, 2.0 g Zn, 1.0 g triphenylphosphine, and 0.16 g 2,2'-bipyridine were placed in a 50 ml flask. The flask was evacuated and filled with nitrogen and then 15 ml of dry DMAC and 2 ml p-chloroanisole were added. The mixture was stirred and reacted at 70° for 45 minutes. Gas chromatographic analysis of the mixture revealed 3.4% anisole, 96.4% dimethoxybiphenyl, and a trace (0.2%) of p-chloroanisole. In contrast to Example 13, higher yield of coupled product was obtained and there were no other biphenyls produced. The reaction was also faster (45 vs. 90 minutes).

EXAMPLE 25

This Example illustrates the use of 2-methylaminopyridine to suppress formation of the monosubstituted product. To a mixture of 0.13 g nickel chloride, 0.8 g triphenylphosphine, 2.0 g zinc dust, and 1.0 g sodium bromide in a 50 ml flask, 10 ml DMF (dimethylformamide) and 0.2 ml 2-methylaminopyridine were added under a nitrogen atmosphere. This mixture was reacted for several minutes at 70° and then 2 ml p-chloroanisole were added. After 5 hours at 70°, gas chromatographic analysis of the reaction mixture revealed: anisole (34.5%), p-chloroanisole (1.4%) and 4,4'-methoxybiphenyl (62.9%). There was also a trace of other biphenyls.

EXAMPLE 26

This Example illustrates that bipyridine can be generated in situ and is as effective at suppressing the monosubstituted product as adding bipyridine to the initial catalyst mixture. To a 50 ml flask were added 0.13 g nickel chloride, 1.0 g triphenylphosphine, 1.0 g sodium bromide and 2.5 g zinc dust. The flask was sealed, evacuated, and then filled with nitrogen. Fifteen ml of dry DMAC were added through a serum cap and the solution was stirred at 70° for several minutes. Two-tenths ml of 2-chloropyridine was added (through the serum cap) and reacted for 45 mins. Two mls of p-chloroanisole were then added and reacted for 2 hours. Gas chromatographic analysis after this period revealed: anisole (7.4%), 4-methoxybiphenyl (0.3%) and 4,4'-dimethoxybiphenyl (92.3%).

EXAMPLE 27

This Example illustrates that a triaryl phosphine need not be present for the coupling reaction to occur, and that bipyridine can be used in its place.

In a 50 ml flask were placed 0.13 g $NiCl_2$, 2.0 Zn, 1.0 g NaI, and 0.62 g bipyridine. After evacuation and filling with nitrogen, 10 ml dry DMAC were added along with 2 ml chlorobenzene. The mixture was stirred and reacted at 80°. After 48 hours there was 78 percent conversion of chlorobenzene to biphenyl.

Although the invention has been described in its preferred form with a certain degree of particularity, it is understood that the present disclosure has been made only by way of example and that numerous changes can be made without departing from the spirit and scope of the invention.

What is claimed is:

1. A method for coupling aryl and heteroaryl mono chlorides having 4 to 30 carbons which comprises contacting said aryl mono chlorides in an aprotic solvent with a catalyst mixture comprising an anhydrous nickel compound and at least one ligand selected from the group consisting of a triaryl phosphine having 6 to about 14 carbons in each aryl moiety and an aromatic bidentate compound containing at least one ring nitrogen atom and about 5 to about 30 carbon atoms in the presence of a reducing metal selected from the group consisting of zinc, magnesium or manganese, at a temperature of about 0° to about 250° C., wherein the ratio of gram atoms of nickel to moles of aryl chloride is in the range of about 0.0001 to about 0.5, the amount of ligand is about 0.1 to about 100 moles per gram atom of nickel and the amount of reducing metal is at least about 0.5 gram atoms per mole of reacted aryl chloride.

2. A method as claimed in claim 1 wherein the reducing metal is a finely divided powder having a mesh size of 20 or finer when measured in the U.S. sieve scale.

3. A method as claimed in claim 1 wherein the nickel compound is nickel chloride.

4. A method as claimed in claim 1 wherein the ligand is a triaryl phosphine.

5. A method as claimed in claim 4 wherein the triaryl phosphine is triphenyl phosphine.

6. A method as claimed in claim 1 wherein the ligand is an aromatic bidentate compound.

7. A method as claimed in claim 6 wherein the aromatic bidentate compound is 2,2'-bipyridine.

8. A method as claimed in claim 1 wherein the ligand is a mixture of triaryl phosphine and an aromatic bidentate compound containing at least one ring nitrogen.

9. A method as claimed in claim 1 wherein at least 0.1 moles per gram atom of nickel of an inorganic salt is added as a promoter.

10. A method as claimed in claim 9 wherein the inorganic salt is an alkali metal iodide.

11. A method as claimed in claim 9 wherein the inorganic salt is an alkali metal bromide.

12. A method as claimed in claim 9 wherein the inorganic salt is alkali metal chloride.

13. A method as claimed in claim 1 wherein the aprotic solvent is dimethylacetamide.

14. A method as claimed in claim 1 wherein the aprotic solvent is dimethyl formamide.

15. A method as claimed in claim 1 wherein the aryl chloride has the formula:

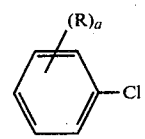

wherein R is a monovalent inert radical selected from the group consisting of alkyl, aryl, F, unsubstituted or substituted amino, —CN, —CHO, —Oaryl, —Oalkyl, —OCO—alkyl, —OCOaryl, —COOalkyl, —COOaryl,

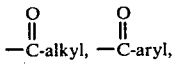

—$SO_2$-alkyl, —$SO_2$aryl, —$SO_3$alkyl, —$SO_3$aryl wherein the aryl contains 4 to about 30 carbons, the alkyl contains 1 to about 8 carbons and a is an integer having values of 0 to 4 with the proviso that no more than one R is in a position ortho to the Cl-containing ring carbon atom.

16. A method as defined in claim 15 wherein one or more of the carbon atoms of the benzene ring in formula (I) is replaced by N or P.

17. A method as claimed in claim 16 wherein the aryl chloride is 2-chloropyridine.

18. A method as claimed in claim 15 wherein R is methyl and a is 1.

19. A method as claimed in claim 15 wherein R is $CH_3CO_2$— and a is 1.

20. A method as claimed in claim 1 wherein the temperature is from about 25° C. to about 120° C.

* * * * *